US006552174B2

(12) United States Patent
Wei et al.

(10) Patent No.: US 6,552,174 B2
(45) Date of Patent: Apr. 22, 2003

(54) HUMAN MUTT2 ANTIBODIES

(75) Inventors: Ying-Fei Wei, Berkeley, CA (US); Ewen F. Kirkness, Olney, MD (US)

(73) Assignee: Human Genome Sciences, Inc., Rockville, MD (US)

(*) Notice: Subject to any disclaimer, the term of this patent is extended or adjusted under 35 U.S.C. 154(b) by 0 days.

(21) Appl. No.: 09/974,800

(22) Filed: Oct. 12, 2001

(65) Prior Publication Data

US 2002/0102588 A1 Aug. 1, 2002

Related U.S. Application Data

(60) Division of application No. 09/432,253, filed on Nov. 2, 1999, now Pat. No. 6,344,547, which is a division of application No. 08/916,989, filed on Aug. 21, 1997, now Pat. No. 6,103,871, which is a division of application No. 08/470,261, filed on Jun. 6, 1995, now Pat. No. 5,695,980, which is a continuation-in-part of application No. PCT/US94/13187, filed on Nov. 15, 1994.

(51) Int. Cl.$^7$ ........................... C07K 16/40; C12N 5/12; G01N 33/53
(52) U.S. Cl. ............................... 530/388.26; 530/387.3; 530/389.1; 530/391.1; 530/391.3; 530/809; 435/7.1; 435/331; 435/346; 424/133.1; 424/135.1
(58) Field of Search ..................... 530/388.26, 387.3, 530/389.1, 391.1, 391.3, 809; 435/7.1, 331, 346; 424/133.1, 135.1

(56) References Cited

U.S. PATENT DOCUMENTS 5,227,471 A   7/1993   Wright, Jr.

FOREIGN PATENT DOCUMENTS

WO    WO 94/13187    11/1994

OTHER PUBLICATIONS

Yang, H. et al., Cloning and characterization of a new member of the nudix hydrolases from human and mouse, The Journal of Biological Chemistry, 2000, pp. 8844–8853, vol. 275, No. 12.
Gasmi, L. et al., Cloning, expression and characterization of YSA1H, a human adenosine 5'–diphosphosugar pyrophosphatase possessing a MutT motif, Biochemical Journal, 1999, pp. 331–337, vol. 344.
NCI–CGAP, Genbank Accession No. AI188576 (Oct. 28, 1998).
Hillier, L. et al., Genbank Accession No. AA775802 (Feb. 5, 1998).
New England Biolabs Catalog, 1986, p. 60, Beverly, MA, USA.
Cross, et al., Purification of CpG islands using a methylated DNA binding column, Nature Genetics, Mar. 1994, pp. 236–244, vol. 6.
Devlin, Textbook of Biochemistry with clinical correlations, A Wiley medical publication, 1982, pp. 986–987.
Sakumi, K. et al., Cloning and expression of a cDNA for a human enzyme that hydrolyzes 8–Oxo–dGTP, a mutagenic substrate for DNA synthesis, The Journal of Biological Chemistry, Nov. 5, 1993, pp. 23524–23530, vol. 268, No. 31.
Mo, J. et al., Hydrolytic elimination of a mutagenic nucleotide, 8–Oxo–dGTP, by human 18–kilodalton protein: Sanitization of nucleotide pool, Proceedings of the National Academy Sciences, Nov. 1992, pp. 11021–11025, vol. 89.
Tchou, J. et al., Repair of DNA containing the oxidatively–damaged base, 8–Oxoguanine, Mutation Research, 1993, pp. 277–287, vol. 299.
Akiyama, M. et al., Molecular cloning and nucleotide sequence of the mutT mutator of *Escherichia coli* that causes A:T to C:G transversion, Molecular and General Genetics, 1987, pp. 9–16, vol. 296.
Maki, H. et al., MutT protein specifically hydrolyses a potent mutagenic substrate for DNA synthesis, Nature, Jan. 16, 1992, pp. 273–275, vol. 355.
GenBank Accession No. HS41H10F (Oct. 23, 1995).
Lathe, R., Synthetic oligonucleotide probes deduced from amino acid sequence data. Theoretical and practical considerations, Journal of Molecular Biology, May 5, 1985, pp. 1–12, vol. 183, No. 1.
Tijan, et al., Cell, 1994, pp. 5–8, vol. 77.
Ranish, et al., Isolation of two genes that encode subunits of the yeast transcription factor IIA, Science, Feb. 28, 1992, pp. 1127–1129, vol. 255, No. 5048.
Corixa Corp., Geneseq Accession No. AAF17719, "Human breast cancer associated 19459–1 coding sequence," Mar. 13, 2001.
Corixa Corp., Geneseq Accession No. AAA06590, "Human immunogenic prostate tumour protein cDNA sequence SEQ ID No.:365," Jun. 13, 2000.
Corixa Corp., Geneseq Accession No. AAA70013, "Human ovarian carcinoma antigen polynucleotide SEQ ID No.:324," Nov. 7, 2000.
Genbank Accession No. NM_014142, "Homo sapiens nudix (nucleoside disphosphate linked moiety X)–type motif 5 (NUDT5)," Nov. 2, 2000.
Genbank Accession No. NP_054861, "nudix (nucleoside diphosphate linked moiety X)–type motif 5 [Homo sapiens]," Nov. 2, 2000.
Ngo et al., 1994, The Protein Folding Problem and Tertiary Structure Prediction, pp. 492–495.*
Kuby et al, 1994, Immunology, Second edition, pp. 86–96.*

\* cited by examiner

*Primary Examiner*—Christina Chan
*Assistant Examiner*—Phuong N. Huynh
(74) *Attorney, Agent, or Firm*—Human Genome Sciences, Inc.

(57) ABSTRACT

A human hMutT2 polypeptide and DNA (RNA) encoding such polypeptide and a procedure for producing such polypeptide by recombinant techniques is disclosed. Also disclosed are methods for utilizing such polypeptide for hydrolyzing and eliminating oxidized guanine nucleotides from the nucleotide pool to ensure correct DNA synthesis. Diagnostic assays are also disclosed which detect the presence of a mutated form of hMutT2 and over-expression of the hMutT2 protein.

78 Claims, 7 Drawing Sheets

```
                                                                              -70
                       -110              -90
TGGCACCGGCATCGGCTGACACTGCTGCCTCCAGCTAGTTATTTCGTCCTCTTCCGTTCT
-----+----+----+----+----+----+----+----+----+----+----+----+
ACCGTGGCCGTAGCCGACTGTGACGACGGAGGTCGATCAATAAAGCAGGAGAAGGCAAGA
                   -50                  -30                  -10
TCACCCCTACACCTTGGAGGTGAACTTCTCACCTGAGGGCTGTAAAGACTCGTTTGAAAA
-----+----+----+----+----+----+----+----+----+----+----+----+
AGTGGGGATGTGGAACCTCCACTTGAAGAGTGGACTCCCGACATTTCTGAGCAAACTTTT
                                                             M
                     10                  30                  50
TGGAGAGCCAAGAAGAACCAACGGAATCTTCTCAGAATGGCAAACAGTATATCATTTCAGAGG
-----+----+----+----+----+----+----+----+----+----+----+----+
ACCTCTCGGTTCTTGGTTGCCTTAGAAGAGTCTTACCGTTTGTCATATAGTAAAGTCTCC
 E  S  Q  E  P  T  E  S  S  Q  N  G  K  Q  Y  I  I  S  E  E
                     70                  90                  110
AGTTAATTTCAGAAGGAAAATGGGTCAAGCTTGAAAAAACAACGTACATGGATCCTACTG
-----+----+----+----+----+----+----+----+----+----+----+----+
TCAATTAAAGTCTTCCTTTTACCCAGTTCGAACTTTTTGTTGCATGTACCTAGGATGAC
 L  I  S  E  G  K  W  V  K  L  E  K  T  T  Y  M  D  P  T  G
                    130                 150                 170
```

FIG. 1A

```
                                                                                GTAAAACTAGAACTTGGGAATCAGTGAACGTACCAACCAGGAAAGAGCAGACTGCGGATG
                                                                                ------------+------------+------------+------------+------------+
                                                                                CATTTGATCTTGAACCCTTAGTCACTTGCATGGTTGGTCCTTTCTCGTCTGACGCCTAC
                                                                                       K  T  R  T  W  E  S  V  N  V  P  T  R  K  E  Q  T  A  D  G
                                                                                                 190                     210                     230

GTGTCGCGGTCATCCCCGTGCTGCAGAGAACACTTCACTATGAGTGTATCGTTCTGGTGA
------------+------------+------------+------------+------------+
CACAGCGCCAGTAGGGGCACGACGTCTCTTGTGAAGTGATACTCACATAGCAAGACCACT
  V  A  V  I  P  V  L  Q  R  T  L  H  Y  E  C  I  V  L  V  K
         250                     270                     290

AACAGTTCCGACACCAATGGGGGCTACTGCATAGAGTTCCCTGCAGGTCTCATAGATG
------------+------------+------------+------------+------------+
TTGTCAAGGCTGTGGTTACCCCCGATGACGTATCTCAAGGACGTCCAGAGTATCTAC
              Q  F  R  P  P  M  G  G  Y  C  I  E  F  P  A  G  L  I  D  D
                        310                     330                     350

ATGGTGAAACCCCAGAAGCAGTCGTCTTCCGGGAGCTTGAAGAAGAAACTGGCTACAAAG
------------+------------+------------+------------+------------+
TACCACTTTGGGGTCTTCGTCAGCAGAAGGCCCTCGAACTTCTTCTTTGACCGATGTTTC
  G  E  T  P  E  A  A  A  L  R  E  L  E  E  E  T  G  Y  K  G
         370                     390                     410

GGGACATTGCCGAATGTTCTCCAGGGTCTGTATGGACCCAGGCTTGTCAAACTGTACTA
```

FIG. 1B

```
-----|----+----|----+----|----+----|----+----|----+----|----+----|----+----|
CCTGTAACGGCTTACAAGAGGTCGCCAGACATACCTGGGTCCGAACAGTTTGACATGAT
 D   I   A   E   C   S   P   A   V   C   M   D   P   G   L   S   N   C   T   I
        430                 450                         470

TACACATCGTGACAGTCACCATTAACGGAGATGATGCCGAAAACGCAAGGCCGAAGCCAA
 H   I   V   T   I   N   G   D   D   A   E   N   A   R   P   K
        490                         510                         530

ATGTGTAGCACTGTCAGTGATGTGGTAATTGCCTCTACTACGGCTTTTGCGTTCCGGCTTCGGT
 P   G   D   G   E   F   V   E   V   I   S   L   P   K   N   D   L   L   Q   R
        550                         570                         590

AGCCAGGGGATGGAGAGTTTGTGGAAGTCATTCTTTACCCAAGAATGACCTGCTGCAGA

TCGGTCCCTACCTCTCAAACACCTTCAGTAGAGTCACCTGCGTCCAGATAAGGATGC
 L   D   A   L   V   A   E   E   H   L   T   V   D   A   R   V   Y   S   Y   A
        610                         630                         650

GACTTGATGCTCTGGTAGCTGAAGAACATCTCACAGTGGACGCCAGGGTCTATTCCTACG

CTGAACTACGAGACCATGCGACTTCTTGTAGAGTGTCACCTGCGGTCCCAGATAAGGATGC

CTCTAGCGCTGAAACATGCAAATGCAAAGCCATTGAAGTGCCCTTCTTGAAATTTTAAG

GAGATCGCGACTTTGTACGTTTCGGTAAACTTCACGGGAAGAACTTTAAAATTC
```

FIG. 1C

```
 L  A  L  K  H  A  N  A  K  P  F  E  V  P  F  L  K  F  *
670                    690                       710
    .         .         .         .         .         .
CCCAAATATGACACTGGCCATTTTTGTAAACGAGACCACCAGGCCTTCTTCACTAAGACT
----+----+----+----+----+----+----+----+----+----+----+----
GGGTTTATACTGTGACCGGTAAAAACATTTGCTCTGGTGGTCCGGAAGAAGTGATTCTGA
       730               750               770
    .         .         .         .         .         .
TTGTATTCAACTTAGTTAATGTAGATTGCCATTAGCTTTTTCGTAAAATAAAAGCACA
----+----+----+----+----+----+----+----+----+----+----+----
AACATAAGTTGAATCAATTACATCTAAACGGTAATCGAAAAAGCATTTTATTTTCGTGT
       790               810               830
    .         .         .         .         .         .
GAACAGATGTGGTGGTGGTATGGAATTGTAATTACAGGTAGGTTGTGACCTTCCTTTAAA
----+----+----+----+----+----+----+----+----+----+----+----
CTTGTCTACACCACCACCATACCTTAACATTAATGTCCATCCAACACTGGAAGGAAATTT
       850               870               890
    .         .         .         .         .         .
TTTGTTATAACTCCAGCTAAAATTAACAAAGAATATAAATGCAAGTATGTTACTCCAAT
----+----+----+----+----+----+----+----+----+----+----+----
AAACAATATTGAGGTCGATTTAATTGTTCTTATATTTACGTTCATACAAATGAGGTTA
```

FIG. 1D

```
         910                930                950
TTTTTTAAAGCTCAACAGAGAGTTAACTACAGCTCAGTTACTTTTCTAGTCCAGTCTGGAAC
----+----|----+----|----+----|----+----|----+----|----+----|
AAAAAATTTCGAGTTGTCTCAATTGATGTCGAGTCAATGAAAAGATCAGGTCAGACCTTG
         970                990                1010

ACAGGGGTATTGGTATTGAGAAATAGACCTGAGTTCTCAATTAGGTCA
----+----|----+----|----+----|----+----|
TGTCCCCATAAACCATAACTCTTTATCTGGACTCAAGAGTTAATCCAGT
```

FIG. 1E

```
                                                                                    eMUTT
                                                                                    hMUTT1
                                                                                    hMUTT2

```
 97  K E G Q P G E W M S L V G L N A D D F P P A N E P V I A K – – – – – – – – –                  eMUTT
 98  S D E M R P C W F Q L D Q I P F K D M W P D D S Y W F P – – L L Q K K F H          hMUTT1
161  K P C D – G E F V E V I S L P K N D L L Q R L D A L V A E E H L T V D A R V Y –    hMUTT2
```
```
                170              180              190              200
```

```
126  – – – – – – – – – – – – – – – – – – – – – – – – – – –                             eMUTT
185  G Y F K F Q G Q D T I L D Y T L R E V D T L                                        hMUTT1
199  S Y A L A L K H A N A K P F E V P F L K F                                          hMUTT2
```
```
                210              220
```

FIG. 2B

HUMAN MUTT2 ANTIBODIES

CROSS REFERENCE TO RELATED APPLICATIONS

This application is a divisional of and claims priority under 35 U.S.C. §120 to U.S. application Ser. No. 09/432,253, filed Nov. 2, 1999 (now U.S. Pat. No. 6,344,547, issued Feb. 5, 2002), which is a divisional of and claims priority under 35 U.S.C. §120 to U.S. application Ser. No. 08/916,989, filed Aug. 21, 1997 (now U.S. Pat. No. 6,103,871, issued Aug. 15, 2000), which is a divisional of and claims priority under 35 U.S.C. §120 to U.S. application Ser. No. 08/470,261, filed Jun. 6, 1995 (now U.S. Pat. No. 5,695,980, issued Dec. 9, 1997), which is a continuation in part of and claims priority under 35 U.S.C. §120 to International Application No. PCT/US94/13187, filed Nov. 15, 1994 (published by the International Bureau in the English language on May 23, 1996 as International Publication No. WO96/15222), all of which are hereby incorporated herein by reference in their entirety.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention is human MutT2, sometimes hereinafter referred to as "hMutT2." The invention also relates to inhibiting the action of such polypeptides.

BACKGROUND OF THE INVENTION

Errors in DNA replication lead to spontaneous mutations. Elevated spontaneous mutations lead directly to abnormal cell growth and disorders, such as tumors. A certain portion of spontaneous mutagenesis is caused by endogenous free radicals which are generated by normal cellular metabolism. The free radicals cause oxidative damage to DNA and may be an important determinant in longevity (Ames, B. N. and Gold, L. S., Mutat. Res., 250:3–16 (1991)).

Oxygen radicals damage chromosomal DNA, causing cell death and inducing mutations. One type of DNA damage caused by oxygen radicals is an oxidized form of the guanine base (8-oxoguanine) (Shibutani, S., et al., Nature, 349:431–4 (1991)). This oxidized form of guanine can pair with cytosine and adenine, and G:C to T:A transversions follow (Tkeshelashvili, L. K., et al., J. Biol. Chem., 266:6401–6406 (1991)). Thus, active oxygen species produced by cellular metabolic intermediates are sufficient to oxidize the guanine base of the DNA, even in normally growing cells.

Oxidation of guanine proceeds also in a form of free nucleotide, and an oxidized form of dGTP, 8-oxo-dGTP, is a potent mutagenic substrate for DNA synthesis (Maki, H. and Sekiguchi, M., Nature, 355:273–275 (1992)). In contrast with the consequence of 8-oxoguanine arising in DNA, 8-oxo-dGTP can induce A:T to C:G as well as G:C to T:A transversions (Cheng, K. C., et al., J. Biol. Chem., 267:166–172 (1992)).

In *E. coli* there are mechanisms that prevent mutations caused by oxidation of the guanine base in both DNA and free nucleotide forms. Oxidized DNA is repaired by the MutM protein, which possesses activity to remove the 8-oxoguanine base from the damaged DNA. On the other hand, 8-oxo-dGTP can be eliminated from the nucleotide pool by the mutT protein, which hydrolyses the mutagenic nucleotide to 8-oxo-dGMP (Maki, H. and Sekiguchi, M., Nature, 355:273–275 (1992)). In the mutT mutant, 8-oxo-dGMP misincorporated opposite to dA residues of template may be removed by the mutM protein before the next round of DNA replication. The mutT protein, therefore, degrades the potent mutagenic substrate, 8-oxo-dGTP to the harmless monophosphate substrate to ensure proper DNA synthesis. Mutations in the *E. coli* mutT gene cause an increase of the occurrence of A:T to C:G transversions 100–10,000-fold over the wild-type level (Akiyama, M., et al., Mol. and Gen. Genet., 206:9–16 (1987)).

Eukaryotes and mammals also have an enzyme which hydrolyses oxidized nucleotides. The enzyme is homologous to the *E. coli* mutT gene. A significant amount of 8-oxoguanine is formed in the chromosome DNA of mammalian cells and most of the damaged nucleotides are excised from the DNA and excreted into the urine (Ames, B. N. and Gold, L. S., Mutat. Res., 250:3–16 (1991) and Shigenaga, M. K., et al., PNAS, 86:9697–9701 (1989)).

The spontaneous oxidation of dGTP forms 8-oxo-dGTP which can be inserted opposite dA and dC residues of template DNA with almost equal efficiency, and the mutT protein specifically degrades 8-oxo-dGTP to the monophosphate. Thus, elimination of the oxidized form of guanine nucleotide from a nucleotide pool is important for the high fidelity of DNA synthesis.

BRIEF SUMMARY OF THE INVENTION

The polypeptide of the present invention corresponds in size and amino acid sequence homology to human MutT and has, therefore, been preliminarily characterized as human MutT2.

In accordance with one aspect of the present invention, there is provided a novel mature polypeptide which is hMutT2, as well as biologically active and diagnostically or therapeutically useful fragments, analogs and derivatives thereof.

In accordance with another aspect of the present invention, there are provided isolated nucleic acid molecules encoding hMutT2, including mRNAs, DNAs, cDNAs, genomic DNA as well as biologically active and diagnostically or therapeutically useful fragments, analogs and derivatives thereof.

In accordance with yet a further aspect of the present invention, there is provided a process for producing such polypeptide by recombinant techniques which comprises culturing recombinant prokaryotic and/or eukaryotic host cells, containing a hMutT2 nucleic acid sequence, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, to prevent and treat diseases associated with errors in DNA replication and abnormal cell growth, for example that present in a tumor and a cancer, by specifically hydrolyzing oxidized nucleoside triphosphates, in particular, 8-oxo-dGTP, to the corresponding monophosphate for high fidelity of DNA synthesis.

In accordance with another aspect of the present invention there are provided nucleic acid probes comprising nucleic acid molecules of sufficient length to specifically hybridize to hMutT2 sequences.

In accordance with yet a further aspect of the present invention, there are provided antibodies against such polypeptides.

In accordance with another aspect of the present invention there is provided a method of diagnosing a disease or a susceptibility to a disease, for example, abnormal cellular growth, related to a mutation in hMutT2 nucleic acid sequences and the protein encoded by such nucleic acid sequences.

In accordance with yet another aspect of the present invention, there are provided antagonists to such polypeptides, which may be used to inhibit the action of such polypeptides, for example, in the treatment of tumors.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1E collectively show the polynucleotide sequence (SEQ ID NO:1) and the corresponding deduced amino acid sequence (SEQ ID NO:2) of hMutT2. The standard one-letter abbreviations for amino acids are used.

FIGS. 2A–2B collectively illustrate an amino acid sequence comparison of *E. coli* MutT (upper line, SEQ ID NO:9), human MutT1 (middle line, SEQ ID NO:10), and hMutT2 (lower line, SEQ ID NO:2) by presenting an alignment of these amino acid sequences. The shaded areas represent amino acid residues which are the same between the different sequences. The standard one-letter abbreviations for amino acids are used. As shown in FIGS. 2A–2B, hMutT2 has a higher amino acid homology to *E. coli* MutT than human MutT1.

DETAILED DESCRIPTION

In accordance with an aspect of the present invention, there are provided isolated nucleic acids (polynucleotide) which encode for the mature polypeptide having the deduced amino acid sequence of FIGS. 1A–1E or for the mature polypeptide encoded by the cDNA of the clone deposited under the terms of the Budapest Treaty with the American Type Culture Collection (ATCC), 10801 University Boulevard, Manassas, Va. 20110–2209, as ATCC Deposit No. 75882 on Aug. 31, 1994.

A polynucleotide encoding a polypeptide of the present invention may be obtained from most human tissues, such as thymus, liver, spleen and prostate. The polynucleotide of this invention was discovered in a cDNA library derived from a human 8 week old embryo. It is structurally related to the hMutT family. It contains an open reading frame encoding a protein of 219 amino acid residues. The protein exhibits the highest degree of homology to *E. coli* MutT with 62% identity and 77% similarity over a 27 amino acid stretch. It is also important that GETXE and RELQ/EEE are conserved among *E. coli* MutT, human MutT1 and hMutT2.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1E or that of the deposited clone or may be a different coding sequence which coding sequence, as a result of the redundancy or degeneracy of the genetic code, encodes the same mature polypeptide as the DNA of FIGS. 1A–1E or the deposited cDNA.

The polynucleotide which encodes for the mature polypeptide of FIGS. 1A–1E or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1E or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1E or the same mature polypeptide encoded by the cDNA of the deposited clone as well as variants of such polynucleotides which variants encode for a fragment, derivative or analog of the polypeptide of FIGS. 1A–1E or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1E or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1E (SEQ ID NO: 1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as a convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a hMutT2 polypeptide which has the deduced amino acid sequence of FIGS. 1A–1E or which has the amino acid sequence encoded by the deposited cDNA, as well as fragments, analogs and derivatives of such polypeptide.

The terms "fragment," "derivative" and "analog" when referring to the polypeptide of FIGS. 1A–1E or that encoded by the deposited cDNA, means a polypeptide which retains essentially the same biological function or activity as such polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1E or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the hMutT2 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmiacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The hMutT2 polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The hMutT2 polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The hMutT2 polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Once the hMutT2 polypeptide is being expressed intracellularly via gene therapy, it hydrolyses the oxidized form of nucleoside triphosphates and has a strong affinity for the oxidized form of guanine nucleotide, therefore eliminating them from the nucleotide pool and ensuring the high fidelity of DNA synthesis. In the absence of the hMutT2 polypeptide, there would be a significant increase in errors in DNA replication which would lead to mutagenesis. Mutagenesis is known to cause numerous disorders, including abnormal cell growth, for example that present in a tumor and a cancer. Accordingly, administration of the polypeptide of the present invention may be used to treat or prevent mutagenesis.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

This invention is also related to the use of the hMutT2 gene as part of a diagnostic assay for detecting diseases or susceptibility to diseases related to the presence of mutated hMutT2. Such diseases are related to errors in DNA replication, for example, such as those which lead to tumors and cancers.

Individuals carrying mutations in the hMutT2 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding hMutT2 can be used to identify and analyze hMutT2 mutations. For example, deletions and insertions can be detected by a change in size of the amplified product in comparison to the normal genotype. Point mutations can be identified by hybridizing amplified DNA to radiolabeled hMutT2 RNA or alternatively, radiolabeled hMutT2 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of hMutT2 protein in various tissues since an over-expression of the proteins compared to normal control tissue samples may detect the presence of a disease or susceptibility to a disease related to errors in DNA replication, for example, a tumor. Assays used to detect levels of hMutT2 protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the hMutT2 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any hMutT2 proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to hMutT2. Unattached reporter antibody is then washed out. Peroxidase substrates are then added to the dish and the amount of color developed in a given time period is a measurement of the amount of hMutT2 protein present in a given volume of patient sample when compared against a standard curve.

A competition assay may be employed wherein antibodies specific to hMutT2 are attached to a solid support and labeled hMutT2 and a sample derived from the host are passed over the solid support and the amount of label detected, for example by liquid scintillation chromatography, can be correlated to a quantity of hMutT2 in the sample.

A "sandwich" assay is similar to an ELISA assay. In a "sandwich" assay hMutT2 is passed over a solid support and binds to antibody attached to a solid support. A second antibody is then bound to the hMutT2. A third antibody which is labeled and specific to the second antibody is then passed over the solid support and binds to the second antibody and an amount can then be quantitated.

The invention also relates to a method of screening compounds to identify those which enhance (agonists) or block (antagonists) the functions of hMutT2. An example of such an assay comprises measuring the hydrolysis of 8-oxo-dGTP to 8-oxo-dGMP in the presence of hMutT2 and the compound to be screened. The reaction mixture (12.5 µl) contains 20 mM Tris·HCl, pH 8.0, 4 mm $MgCl_2$, 40 mM NaCl, 20 µM 8-oxo-dGTP, 80 µg/ml bovine serum albumin, 8 mM DTT, 10% glycerol, hMutT2 and the compound to be screened. The reaction is run at 30° C. for 20 minutes and stopped by adding 2.0 µl of 50 mm EDTA. An aliquot (2 µl) of the reaction mixture was spotted on a polyethyleneimine-cellulose plate, and the product is separated from the substrate by TLC with 1M LiCl for one hour and quantitated by autoradiographic analysis with a Fujix Bio-image analyzer (Fuji Photofilm Company Limited Tokyo). The ability of the compound to inhibit or enhance the action of hMutT2 is then analyzed.

Human MutT2 is produced and functions intra-cellularly, therefore, any antagonists must be intra-cellular. Potential antagonists to hMutT2 include antibodies which are produced intra-cellularly. For example, an antibody identified as antagonizing hMutT2 may be produced intra-cellularly as a single chain antibody by procedures known in the art, such as transforming the appropriate cells with DNA encoding the single chain antibody to prevent the function of hMutT2.

Another potential hMutT2 antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of hMutT2. The antisense RNA oligonucleotide hybridizes to the mRNA in vivo and blocks translation of the mRNA molecule into the hMutT2 polypeptide (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of hMutT2.

Potential hMutT2 antagonists also include a small molecule, which are able to pass through the cell membrane, and bind to and occupy the catalytic site of the polypeptide thereby making the catalytic site inaccessible to substrate such that normal biological activity is prevented. Examples of small molecules include but are not limited to small peptides or peptide-like molecules.

The antagonists may be employed to target undesired cells, e.g., abnormally differentiating cells such as in tumors and cancers, since the prevention of hMutT2 activity prevent corrections in DNA replication errors, and may lead to the destruction of the cell.

The antagonists may be employed in a composition with a pharmaceutically acceptable carrier, e.g., as hereinafter described.

The small molecule agonists and antagonists of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975,. Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of hMutT2

The DNA sequence encoding hMutT2, ATCC #75882, is initially amplified using PCR oligonucleotide primers corresponding to the 5' sequence of the hMutT2 protein (minus the signal peptide sequence) and the vector sequences 3' to the hMutT2 gene. Additional nucleotides corresponding to hMutT2 were added to the 5' and 3' sequences respectively. The 5' oligonucleotide primer has the sequence 5' GCG-GTCGACATGAGCCAAGAACCAACG 3' (SEQ ID NO:3) contains a SalI restriction enzyme site followed by 21 nucleotides of hMutT2 coding sequence starting from the presumed terminal amino acid of the processed protein. The 3' sequence 5' GCGTCTAGATTAAAATTTCAA-GAAGGGCAC 3' (SEQ ID NO:4) contains complementary sequences to XbaI site and is followed by 21 nucleotides of hMutT2. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp'), a bacterial origin of replication (ori), an IPTG-regulatable promoter operator (P/O), a ribosome binding site (RBS), a 6-His tag and restriction enzyme sites. pQE-9 was then digested with SalI and XbaI. The amplified sequences were ligated into pQE-9 and were inserted in frame with the sequence encoding for the histidine tag and the RBS. The ligation mixture was then used to transform E. coli strain m15/REP4 (Qiagen) by the procedure described in Sambrook, J. et al., Molecular Cloning: A Laboratory Manual, Cold Spring Laboratory Press, (1989). m15/REP4 contains multiple copies of the plasmid pREP4, which expresses the lacI repressor and also confers kanamycin resistance (Kan'). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 µg/ml) and Kan (25 µg/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized hMutT2 was purified from this solution by chromatography on a Nickel-Chelate column under conditions that allow for tight binding by proteins containing the 6-His tag (Hochuli, E. et al., J. Chromatography 411:177–184 (1984)). hMutT2 (more than 80% pure) was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Cloning and Expression of hMutT2 using the Haculovirus Expression System

The DNA sequence encoding the full length hMutT2 protein, ATCC #75882, was amplified using PCR oligonucleotide primers corresponding to the 5' and 3' sequences of the gene:

The 5' primer has the sequence 5' GCGCCCGG-GATAAGCCAAGAACCAACG 3' (SEQ ID NO:5) and contains a SmaI restriction enzyme site (underlined) followed by 21 nucleotides resembling an efficient signal for the initiation of translation in eukaryotic cells (J. Mol. Biol. 1987, 196, 947–950, Kozak, M.).

The 3' primer has the sequence 5' GCGGGTACCT-TAAAATTTCAAGAAGGGCAC 3' (SEQ ID NO:6) and contains the cleavage site for the restriction endonuclease Asp718 and 21 nucleotides complementary to the 3' non-translated sequence of the hMutT2 gene. The amplified sequences were isolated from a 1% agarose gel using a commercially available kit ("Geneclean," BIO 101 Inc., La Jolla, Calif.). The fragment was then digested with the endonucleases SmaI and Asp718 and then purified again on a 1% agarose gel. This fragment is designated F2.

The vector pA2 (modification of pVL941 vector, discussed below) is used for the expression of the hMutT2 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases SmaI and Asp718. The polyadenylation site of the simian virus (SV)40 is used for efficient polyadenylation. For an easy selection of recombinant viruses the beta-galactosidase gene from E. coli is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes SmaI and Asp718 and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E. coli HB101 cells were then transformed and bacteria identified that contained the plasmid (pBac hMutT2) with the hMutT2 gene using the enzymes SmaI and Asp718. The sequence of the cloned fragment was confirmed by DNA sequencing.

5 µg of the plasmid pBac hMutT2 was cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBac hMutT2 were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 µL of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-hMutT2 at a multiplicity of infection (MOI) of 2. Six hours later the medium was removed and replaced with SF900 II medium minus methionine and cysteine (Life Technologies Inc., Gaithersburg). 42 hours later 5 $\mu$Ci of $^{35}$S-methionine and 5 $\mu$Ci $^{35}$S cysteine (Amersham) were added. The cells were further incubated for 16 hours before they were harvested by centrifugation and the labelled proteins visualized by SDS-PAGE and autoradiography.

EXAMPLE 3

Expression of Recombinant hMutT2 in COS cells

The expression of plasmid, hMutT2 HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire hMutT2 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding hMutT2, ATCC #75882, was constructed by PCR on the original EST cloned using two primers: the 5' primer 5' GCGGAATTCATGGAGAGC-CAAGAACCAACG 3' (SEQ ID NO:7) contains a EcoRI site followed by 21 nucleotides of hMutT2 coding sequence starting from the initiation codon; the 3' sequence 5' GCGCTCGAGTCAAGCGTAGTCTGG-GACGTCGTATGGGTAAAATTTCAAGAAGG GCAC 3' (SEQ ID NO:8) contains complementary sequences to XhoI site, translation stop codon, HA tag and the last 18 nucleotides of the hMutT2 coding sequence (not including the stop codon). Therefore, the PCR product contains a EcoRI site, hMutT2 coding sequence followed by HA tag fused in frame, a translation termination stop codon next to the HA tag, and an XhoI site. The PCR amplified DNA fragment, and the vector, pcDNAI/Amp, were digested with EcoRI and XhoI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant hMutT2, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the hMutT2 HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 4

Expression Pattern of hMutT2 in Human Tissue

Northern blot analysis was carried out to examine the levels of expression of hMutT2 in human tissues. Total cellular RNA samples were isolated with RNAzol™ B system (Biotecx Laboratories, Inc. 6023 South Loop East, Houston, Tex. 77033). About 15 $\mu$g of total RNA isolated from each human tissue specified was separated on 1% agarose gel and blotted onto a nylon filter. (Sambrook, Fritsch, and Maniatis, Molecular Cloning, Cold Spring Harbor Press, (1989)). The labeling reaction was done according to the Stratagene Prime-It kit with 50 ng DNA fragment. The labeled DNA was purified with a Select-G-50 column. (5 Prime—3 Prime, Inc. 5603 Arapahoe Road, Boulder, Colo. 80303). The filter was then hybridized with radioactive labeled full length hMutT2 gene at 1,000,000 cpm/ml in 0.5M NaPO$_4$, pH 7.4 and 7% SDS overnight at 65° C. The filter was then washed twice at room temperature and twice at 60° C. with 0.5×SSC, 0.1% SDS, and then exposed at -70° C. overnight with an intensifying screen. The message RNA for hMutT2 is abundant in thymus, testis, gall bladder, kidney, liver, lung, spleen, prostate, placenta.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

SEQUENCE LISTING

```
<160> NUMBER OF SEQ ID NOS: 10

<210> SEQ ID NO 1
<211> LENGTH: 1129
<212> TYPE: DNA
<213> ORGANISM: Homo sapiens
<220> FEATURE:
<221> NAME/KEY: CDS
<222> LOCATION: (120)..(779)
<223> OTHER INFORMATION:

<400> SEQUENCE: 1
tggcaccggc atcggctgac actgctgcct ccagctagtt atttcgtcct cttccgttct    60
tcacccctac accttggagg tgaacttctc acctgagggc tgtaaagact cgtttgaaa    119 atg gag agc caa gaa cca acg gaa tct tct cag aat ggc aaa cag tat    167
Met Glu Ser Gln Glu Pro Thr Glu Ser Ser Gln Asn Gly Lys Gln Tyr
1               5                   10                  15 atc att tca gag gag tta att tca gaa gga aaa tgg gtc aag ctt gaa    215
Ile Ile Ser Glu Glu Leu Ile Ser Glu Gly Lys Trp Val Lys Leu Glu
            20                  25                  30 aaa aca acg tac atg gat cct act ggt aaa act aga act tgg gaa tca    263
Lys Thr Thr Tyr Met Asp Pro Thr Gly Lys Thr Arg Thr Trp Glu Ser
        35                  40                  45 gtg aac gta cca acc agg aaa gag cag act gcg gat ggt gtc gcg gtc    311
Val Asn Val Pro Thr Arg Lys Glu Gln Thr Ala Asp Gly Val Ala Val
    50                  55                  60 atc ccc gtg ctg cag aga aca ctt cac tat gag tgt atc gtt ctg gtg    359
Ile Pro Val Leu Gln Arg Thr Leu His Tyr Glu Cys Ile Val Leu Val
65                  70                  75                  80 aaa cag ttc cga cca cca atg ggg ggc tac tgc ata gag ttc cct gca    407
Lys Gln Phe Arg Pro Pro Met Gly Gly Tyr Cys Ile Glu Phe Pro Ala
                85                  90                  95 ggt ctc ata gat gat ggt gaa acc cca gaa gca gct gct ctc cgg gag    455
Gly Leu Ile Asp Asp Gly Glu Thr Pro Glu Ala Ala Ala Leu Arg Glu
            100                 105                 110 ctt gaa gaa gaa act ggc tac aaa ggg gac att gcc gaa tgt tct cca    503
Leu Glu Glu Glu Thr Gly Tyr Lys Gly Asp Ile Ala Glu Cys Ser Pro
        115                 120                 125 gcg gtc tgt atg gac cca ggc ttg tca aac tgt act ata cac atc gtg    551
Ala Val Cys Met Asp Pro Gly Leu Ser Asn Cys Thr Ile His Ile Val
    130                 135                 140
```

```
aca gtc acc att aac gga gat gat gcc gaa aac gca agg ccg aag cca      599
Thr Val Thr Ile Asn Gly Asp Asp Ala Glu Asn Ala Arg Pro Lys Pro
145                 150                 155                 160 aag cca ggg gat gga gag ttt gtg gaa gtc att tct tta ccc aag aat      647
Lys Pro Gly Asp Gly Glu Phe Val Glu Val Ile Ser Leu Pro Lys Asn
                165                 170                 175 gac ctg ctg cag aga ctt gat gct ctg gta gct gaa gaa cat ctc aca      695
Asp Leu Leu Gln Arg Leu Asp Ala Leu Val Ala Glu Glu His Leu Thr
            180                 185                 190 gtg gac gcc agg gtc tat tcc tac gct cta gcg ctg aaa cat gca aat      743
Val Asp Ala Arg Val Tyr Ser Tyr Ala Leu Ala Leu Lys His Ala Asn
        195                 200                 205 gca aag cca ttt gaa gtg ccc ttc ttg aaa ttt taa gcccaaatat           789
Ala Lys Pro Phe Glu Val Pro Phe Leu Lys Phe
    210                 215 gacactggcc attttgtaa acgagaccac caggccttct tcactaagac tttgtattca     849
acttagttta atgtagattt gccattagct ttttcgtaaa ataaaagcac agaacagatg    909
tggtggtggt atggaattgt aattacaggt aggttgtgac cttcctttaa atttgttata    969
actccagcta aaattaacaa agaatataaa tgcaagtatg tttactccaa ttttttttaaa  1029 gctcaacaga gttaactaca gctcagttac ttttctagtc cagtctggaa cacaggggta   1089
tttggtattg agaaatagac ctgagttctc aattaggtca                         1129
```

<210> SEQ ID NO 2
<211> LENGTH: 219
<212> TYPE: PRT
<213> ORGANISM: Homo sapiens

<400> SEQUENCE: 2

```
Met Glu Ser Gln Glu Pro Thr Glu Ser Ser Gln Asn Gly Lys Gln Tyr
1               5                   10                  15

Ile Ile Ser Glu Glu Leu Ile Ser Glu Gly Lys Trp Val Lys Leu Glu
                20                  25                  30

Lys Thr Thr Tyr Met Asp Pro Thr Gly Lys Thr Arg Thr Trp Glu Ser
            35                  40                  45

Val Asn Val Pro Thr Arg Lys Glu Gln Thr Ala Asp Gly Val Ala Val
        50                  55                  60

Ile Pro Val Leu Gln Arg Thr Leu His Tyr Glu Cys Ile Val Leu Val
65                  70                  75                  80

Lys Gln Phe Arg Pro Pro Met Gly Gly Tyr Cys Ile Glu Phe Pro Ala
                85                  90                  95

Gly Leu Ile Asp Asp Gly Glu Thr Pro Glu Ala Ala Leu Arg Glu
            100                 105                 110

Leu Glu Glu Glu Thr Gly Tyr Lys Gly Asp Ile Ala Glu Cys Ser Pro
        115                 120                 125

Ala Val Cys Met Asp Pro Gly Leu Ser Asn Cys Thr Ile His Ile Val
130                 135                 140

Thr Val Thr Ile Asn Gly Asp Asp Ala Glu Asn Ala Arg Pro Lys Pro
145                 150                 155                 160

Lys Pro Gly Asp Gly Glu Phe Val Glu Val Ile Ser Leu Pro Lys Asn
                165                 170                 175

Asp Leu Leu Gln Arg Leu Asp Ala Leu Val Ala Glu Glu His Leu Thr
            180                 185                 190

Val Asp Ala Arg Val Tyr Ser Tyr Ala Leu Ala Leu Lys His Ala Asn
        195                 200                 205
```

```
Ala Lys Pro Phe Glu Val Pro Phe Leu Lys Phe
    210                 215
```

<210> SEQ ID NO 3
<211> LENGTH: 27
<212> TYPE: DNA
<213> ORGANISM: Artificial sequence
<220> FEATURE:
<223> OTHER INFORMATION: Contains a SalI restriction enzyme site

<400> SEQUENCE: 3
gcggtcgaca tgagccaaga accaacg                                           27

<210> SEQ ID NO 4
<211> LENGTH: 30
<212> TYPE: DNA
<213> ORGANISM: Artificial sequence
<220> FEATURE:
<223> OTHER INFORMATION: Contains complementary sequences to XbaI site

<400> SEQUENCE: 4
gcgtctagat taaaatttca agaagggcac                                        30

<210> SEQ ID NO 5
<211> LENGTH: 27
<212> TYPE: DNA
<213> ORGANISM: Artificial sequence
<220> FEATURE:
<223> OTHER INFORMATION: Contains a SmaI restriction enzyme site
      (underlined) followed by 21 nucleotides resembling an efficient
      signal for the initiation of translation in eukaryotic cells (J.
      Mol. Biol. 1987, 196, 947-950, Kozak, M.)

<400> SEQUENCE: 5
gcgcccggga taagccaaga accaacg                                           27

<210> SEQ ID NO 6
<211> LENGTH: 30
<212> TYPE: DNA
<213> ORGANISM: Artificial sequence
<220> FEATURE:
<223> OTHER INFORMATION: Contains the cleavage site for the restriction
      endonuclease Asp718

<400> SEQUENCE: 6
gcgggtacct taaaatttca agaagggcac                                        30

<210> SEQ ID NO 7
<211> LENGTH: 30
<212> TYPE: DNA
<213> ORGANISM: Artificial sequence
<220> FEATURE:
<223> OTHER INFORMATION: Contains a EcoRI site

<400> SEQUENCE: 7
gcggaattca tggagagcca agaaccaacg                                        30

<210> SEQ ID NO 8
<211> LENGTH: 57
<212> TYPE: DNA
<213> ORGANISM: Artificial sequence
<220> FEATURE:
<223> OTHER INFORMATION: Contains complementary sequences to XhoI site,
      translation stop codon, and an HA tag

<400> SEQUENCE: 8
gcgctcgagt caagcgtagt ctgggacgtc gtatgggtaa aatttcaaga agggcac         57

-continued

```
<210> SEQ ID NO 9
<211> LENGTH: 129
<212> TYPE: PRT
<213> ORGANISM: Escherichia coli

<400> SEQUENCE: 9

Met Lys Lys Leu Gln Ile Ala Val Gly Ile Ile Arg Asn Glu Asn Asn
1               5                   10                  15

Glu Ile Phe Ile Thr Arg Arg Ala Ala Asp Ala His Met Ala Asn Lys
            20                  25                  30

Leu Glu Phe Pro Gly Gly Lys Ile Glu Met Gly Glu Thr Pro Glu Gln
        35                  40                  45

Ala Val Val Arg Glu Leu Gln Glu Glu Val Gly Ile Thr Pro Gln His
    50                  55                  60

Phe Ser Leu Phe Glu Lys Leu Glu Tyr Glu Phe Pro Asp Arg His Ile
65                  70                  75                  80

Thr Leu Trp Phe Trp Leu Val Glu Arg Trp Glu Gly Glu Pro Trp Gly
                85                  90                  95

Lys Glu Gly Gln Pro Gly Glu Trp Met Ser Leu Val Gly Leu Asn Ala
            100                 105                 110

Asp Asp Phe Pro Pro Ala Asn Glu Pro Val Ile Ala Lys Leu Lys Arg
        115                 120                 125

Leu

<210> SEQ ID NO 10
<211> LENGTH: 156
<212> TYPE: PRT
<213> ORGANISM: Homo sapiens

<400> SEQUENCE: 10

Met Gly Ala Ser Arg Leu Tyr Thr Leu Val Leu Val Leu Gln Pro Gln
1               5                   10                  15

Arg Val Leu Leu Gly Met Lys Lys Arg Gly Phe Gly Ala Gly Arg Trp
            20                  25                  30

Asn Gly Phe Gly Gly Lys Val Gln Glu Gly Glu Thr Ile Glu Asp Gly
        35                  40                  45

Ala Arg Arg Glu Leu Gln Glu Glu Ser Gly Leu Thr Val Asp Ala Leu
    50                  55                  60

His Lys Val Gly Gln Ile Val Phe Glu Phe Val Gly Glu Pro Glu Leu
65                  70                  75                  80

Met Asp Val His Val Phe Cys Thr Asp Ser Ile Gln Gly Thr Pro Val
                85                  90                  95

Glu Ser Asp Glu Met Arg Pro Cys Trp Phe Gln Leu Asp Gln Ile Pro
            100                 105                 110

Phe Lys Asp Met Trp Pro Asp Asp Ser Tyr Trp Phe Pro Leu Leu Leu
        115                 120                 125

Gln Lys Lys Lys Phe His Gly Tyr Phe Lys Phe Gln Gly Gln Asp Thr
    130                 135                 140

Ile Leu Asp Tyr Thr Leu Arg Glu Val Asp Thr Leu
145                 150                 155
```

What is claimed is:

1. An isolated antibody or fragment thereof that specifically binds to a protein selected from the group consisting of:

(a) a protein consisting of amino acid residues 1 to 219 of SEQ ID NO:2;

(b) a protein consisting of a portion of SEQ ID NO:2, wherein said portion consists of at least 30 contiguous amino acid residues of SEQ ID NO:2 wherein said protein has human MutT2 activity; and (c) a protein consisting of a portion of SEQ ID) NO:2, wherein said portion consists of at least 50 contiguous amino acid residues of SEQ ID NO:2 wherein said protein has human MutT2 activity.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 2 that specifically binds protein (b).

6. The antibody or fragment thereof of claim 2 wherein said protein bound by said antibody or fragment thereof is glycosylated.

7. The antibody or fragment thereof of claim 2 which is a human antibody.

8. The antibody or fragment thereof of claim 2 which is a polyclonal antibody.

9. The antibody or fragment thereof of claim 2 which is selected from the group consisting of:
   (a) a chimeric antibody;
   (b) a humanized antibody;
   (c) a single chain antibody; and
   (d) a Fab fragment.

10. A labeled antibody or fragment thereof wherein the antibody or fragment thereof of claim 2 is labeled.

11. The labeled antibody or fragment thereof of claim 10 wherein the label is selected from the group consisting of:
    (a) an enzyme;
    (b) a fluorescent label; and
    (c) a radiolabel.

12. The antibody or fragment thereof of claim 2 wherein said antibody or fragment thereof specifically binds to said protein in a Western blot.

13. The antibody or fragment thereof of claim 2 wherein said antibody or fragment thereof specifically binds to said protein in an ELISA.

14. A hybridoma that produces the antibody of claim 2.

15. A method of detecting a protein comprising:
    (a) contacting a biological sample with the antibody or fragment thereof of claim 2; and
    (b) detecting the protein.

16. The method of claim 15 wherein the antibody or fragment thereof is a polyclonal antibody.

17. An isolated antibody or fragment thereof obtained from an animal that has been immunized with a protein selected from the group consisting of:
    (a) a protein comprising the amino acid sequence of amino acid residues 1 to 219 of SEQ ID NO:2;
    (b) a protein consisting of the amino acid sequence of at least 30 contiguous amino acid residues of SEQ ID NO:2 wherein said protein has human MutT2 activity; and
    (c) a protein consisting of the amino acid sequence of at least 50 contiguous amino acid residues of SEQ ID NO:2 wherein said protein has human MutT2 activity; wherein said antibody or fragment thereof specifically binds to said amino acid sequence.

18. The antibody or fragment thereof of claim 17 obtained from an animal immunized with protein (a).

19. The antibody or fragment thereof of claim 17 obtained from an animal immunized with protein (b).

20. The antibody or fragment thereof of claim 17 obtained from an animal immunized with protein (c).

21. The antibody or fragment thereof of claim 17 which is a monoclonal antibody.

22. The antibody or fragment thereof of claim 17 which is selected from the group consisting of:
    (a) a chimeric antibody;
    (b) a polyclonal antibody;
    (c) a humanized antibody;
    (d) a single chain antibody; and
    (e) a Fab fragment.

23. An isolated monoclonal antibody or fragment thereof that specifically binds to a protein selected from the group consisting of:
    (a) a protein consisting of amino acid residues 1 to 219 of SEQ ID NO:2;
    (b) a protein consisting of a portion of SEQ ID NO:2, wherein said portion consists of at least 30 contiguous amino acid residues of SEQ ID NO:2 wherein said protein has human MutT2 activity; and
    (c) a protein consisting of a portion of SEQ ID NO:2, wherein said portion consists of at least 50 contiguous amino acid residues of SEQ ID NO:2 wherein said protein has human MutT2 activity.

24. The antibody or fragment thereof of claim 23 that specifically binds protein (a).

25. The antibody or fragment thereof of claim 23 that specifically binds protein (b).

26. The antibody or fragment thereof of claim 23 that specifically binds protein (c).

27. The antibody or fragment thereof of claim 24 that specifically binds protein (b).

28. The antibody or fragment thereof of claim 24 wherein said protein bound by said antibody or fragment thereof is glycosylated.

29. The antibody or fragment thereof of claim 24 which is a human antibody.

30. The antibody or fragment thereof of claim 24 which is selected from the group consisting of:
    (a) a chimeric antibody;
    (b) a humanized antibody;
    (c) a single chain antibody; and
    (d) a Fab fragment.

31. A labeled antibody or fragment thereof wherein the antibody or fragment thereof of claim 24 is labeled.

32. The labeled antibody or fragment thereof of claim 31 wherein the label is selected from the group consisting of:
    (a) an enzyme;
    (b) a fluorescent label; and
    (c) a radiolabel.

33. The antibody or fragment thereof of claim 24 wherein said antibody or fragment thereof specifically binds to said protein in a Western blot.

34. The antibody or fragment thereof of claim 24 wherein said antibody or fragment thereof specifically binds to said protein in an ELISA.

35. A hybridoma that produces the antibody or fragment thereof of claim 24.

36. A method of detecting a protein comprising:
    (a) contacting a biological sample with the antibody or fragment thereof of claim 24; and
    (b) detecting the protein.

37. An isolated antibody or fragment thereof that specifically binds to a protein selected from the group consisting of:
    (a) a protein consisting of the full-length polypeptide encoded by the HE8AW20 cDNA contained in ATCC Deposit Number 75882;

(b) a protein consisting of a portion of the polypeptide encoded by the HE8AW20 cDNA contained in ATCC Deposit Number 75882, wherein said portion consists of at least 30 contiguous amino acid residues of the polypeptide encoded by the HE8AW20 cDNA contained in ATCC Deposit Number 75882 wherein said protein has human MutT2 activity; and (c) a protein consisting of a portion of the polypeptide encoded by the HE8AW20 cDNA contained in ATCC Deposit Number 75882, wherein said portion consists of at least 50 contiguous amino acid residues of the polypeptide encoded by the HE8AW20 cDNA contained in ATCC Deposit Number 75882 wherein said protein has human MutT2 activity.

38. The antibody or fragment thereof of claim 37 that specifically binds protein (a).

39. The antibody or fragment thereof of claim 37 that specifically binds protein (b).

40. The antibody or fragment thereof of claim 37 that specifically binds protein (c).

41. The antibody or fragment thereof of claim 38 that specifically binds protein (b).

42. The antibody or fragment thereof of claim 38 wherein said protein bound by said antibody or fragment thereof is glycosylated.

43. The antibody or fragment thereof of claim 38 which is a human antibody.

44. The antibody or fragment thereof of claim 38 which is a polyclonal antibody.

45. The antibody or fragment thereof of claim 32 which is selected from the group consisting of:
   (a) a chimeric antibody;
   (b) a humanized antibody;
   (c) a single chain antibody; and
   (d) a Fab fragment.

46. A labeled antibody or fragment thereof wherein the antibody or fragment thereof of claim 38 is labeled.

47. The labeled antibody or fragment thereof of claim 46 wherein the label is selected from the group consisting of:
   (a) an enzyme;
   (b) a fluorescent label; and
   (c) a radiolabel.

48. The antibody or fragment thereof of claim 38 wherein said antibody or fragment thereof specifically binds to said protein in a Western blot.

49. The antibody or fragment thereof of claim 38 wherein said antibody or fragment thereof specifically binds to said protein in an ELISA.

50. A hybridoma that produces the antibody of claim 38.

51. A method of detecting a protein comprising:
   (a) contacting a biological sample with the antibody or fragment thereof of claim 38; and
   (b) detecting the protein.

52. The method of claim 51 wherein the antibody or fragment thereof is a polyclonal antibody.

53. An isolated antibody or fragment thereof obtained from an animal that has been immunized with a protein selected from the group consisting of:
   (a) a protein consisting of the amino acid sequence of the full-length polypeptide encoded by the HE8AW20 cDNA contained in ATCC Deposit Number 75882;
   (b) a protein consisting of the amino acid sequence of at least 30 contiguous amino acid residues of the polypeptide encoded by the HE8AW20 cDNA contained in ATCC Deposit Number 75882 wherein said protein has human MutT2 activity; and (c) a protein consisting of the amino acid sequence of at least 50 contiguous amino acid residues of the polypeptide encoded by the HE8AW20 cDNA contained in ATCC Deposit Number 75882 wherein said protein has human MutT2 activity;
   wherein said antibody or fragment thereof specifically binds to said amino acid sequence.

54. The antibody or fragment thereof of claim 53 obtained from an animal immunized with protein (a).

55. The antibody or fragment thereof of claim 53 obtained from an animal immunized with protein (b).

56. The antibody or fragment thereof of claim 53 obtained from an animal immunized with protein (c).

57. The antibody or fragment thereof of claim 53 which is a monoclonal antibody.

58. The antibody or fragment thereof of claim 53 which is selected from the group consisting of:
   (a) a chimeric antibody;
   (b) a polyclonal antibody;
   (c) a humanized antibody;
   (d) a single chain antibody; and
   (e) a Fab fragment.

59. An isolated monoclonal antibody or fragment thereof that specifically binds to a protein selected from the group consisting of:
   (a) a protein consisting of the full-length polypeptide encoded by the HE8AW20 cDNA contained in ATCC Deposit Number 75882;
   (b) a protein consisting of a portion of the polypeptide encoded by the HE8AW20 cDNA contained in ATCC Deposit Number 75882, wherein said portion consists of at least 30 contiguous amino acid residues of the polypeptide encoded by the HE8AW20 cDNA contained in ATCC Deposit Number 75882 wherein said protein has human MutT2 activity; and
   (c) a protein consisting of a portion of the polypeptide encoded by the HE8AW20 cDNA contained in ATCC Deposit Number 75882, wherein said portion consists of at least 50 contiguous amino acid residues of the polypeptide encoded by the HE8AW20 cDNA contained in ATCC Deposit Number 75882 wherein said protein has human MutT2 activity.

60. The antibody or fragment thereof of claim 59 that specifically binds protein (a).

61. The antibody or fragment thereof of claim 59 that specifically binds protein (b).

62. The antibody or fragment thereof of claim 59 that specifically binds protein (c).

63. The antibody or fragment thereof of claim 60 that specifically binds protein (b).

64. The antibody or fragment thereof of claim 60 wherein said protein bound by said antibody or fragment thereof is glycosylated.

65. The antibody or fragment thereof of claim 60 which is a human antibody.

66. The antibody or fragment thereof of claim 60 which is selected from the group consisting of:
   (a) a chimeric antibody;
   (b) a humanized antibody;
   (c) a single chain antibody; and
   (d) a Fab fragment.

67. A labeled antibody or fragment thereof wherein the antibody or fragment thereof of claim 60 is labeled.

68. The labeled antibody or fragment thereof of claim 67 wherein the label is selected from the group consisting of:

(a) an enzyme;

(b) a fluorescent label; and (c) a radiolabel.

69. The antibody or fragment thereof of claim 60 wherein said antibody or fragment thereof specifically binds to said protein in a Western blot.

70. The antibody or fragment thereof of claim 60 wherein said antibody or fragment thereof specifically binds to said protein in an ELISA.

71. A hybridoma that produces the antibody of claim 60.

72. A method of detecting a protein comprising:

(a) contacting a biological sample with the antibody or fragment thereof of claim 60; and (b) detecting the protein.

73. An isolated antibody or fragment thereof that specifically binds a human MutT2 protein purified from a cell culture wherein the cells in said cell culture comprise a polynucleotide encoding amino acids 1 to 219 of SEQ ID NO:2 operably associated with a regulatory sequence that controls the expression of said polynucleotide.

74. The antibody or fragment thereof of claim 73 which is a monoclonal antibody.

75. The antibody or fragment thereof of claim 73 which is a human antibody.

76. The antibody or fragment thereof of claim 73 which is selected from the group consisting of:

(a) a chimeric antibody;

(b) a polyclonal antibody;

(c) a humanized antibody;

(d) a single chain antibody; and (e) a Fab fragment.

77. The antibody or fragment thereof of claim 73 wherein said antibody or fragment thereof specifically binds to said protein in a Western blot.

78. The antibody or fragment thereof of claim 73 wherein said antibody or fragment thereof specifically binds to said protein in an ELISA.

* * * * *